United States Patent [19]
Delfiner

[11] Patent Number: 4,928,398
[45] Date of Patent: May 29, 1990

[54] ANTHROPOMETER

[76] Inventor: Michael Delfiner, 33 Harold St., Sharon, Mass. 02067

[21] Appl. No.: 335,765

[22] Filed: Apr. 10, 1989

[51] Int. Cl.⁵ ............................................... G01B 5/00
[52] U.S. Cl. ....................................................... 33/512
[58] Field of Search .............. 33/512; 73/432.1, 865.8

[56] References Cited

U.S. PATENT DOCUMENTS

| | | | |
|---|---|---|---|
| 2,215,884 | 9/1940 | Rurge | 33/512 |
| 3,722,103 | 3/1973 | Gregoire | 33/512 X |
| 3,753,293 | 8/1973 | Branda et al. | 33/512 X |
| 4,635,367 | 1/1987 | Vigede | 33/512 X |
| 4,750,268 | 6/1988 | Ravid | 33/512 X |

*Primary Examiner*—Tom Noland
*Attorney, Agent, or Firm*—Wolf, Greenfield & Sacks

[57] ABSTRACT

An anthropometer for the rapid and accurate measurement of dimensions of the human body required for the proper selection of a bicycle. The device includes a support having an upright portion. It also includes a horizontal measuring element adapted to bear against the crotch of a standing individual to be measured which is substantially freely vertically movably attached to the upright portion of the support. The measuring element is urged against the crotch of the individual being measured with a predetermined force to assure accurate measurement without embarrassment to the individual being measured or to the individual performing the measurements.

9 Claims, 2 Drawing Sheets

ANTHROPOMETER

BACKGROUND

I. Field of Invention

The present invention relates to anthropometers, i.e. devices for measuring the human body. More particularly, the invention is directed to devices for accurately determining the bodily measurements of individuals which are necessary to the proper selection of a bicycle.

II. Summary of the Prior Art

Bicycle manufacturers mass-produce bicycles in a few sizes designed to fit riders of "average" proportions. Built-in adjustments permit such mass produced bicycles to be modified for those riders who do not fit the "average" criteria. However, the selection of an appropriately sized bicycle, and its adjustment to the needs of the prospective rider, historically have been based primarily upon guesswork by retail salesmen and/or prospective users. Further, in the selection and adjustment of new bicycles, individuals tend to utilize their customary riding positions. Since the customary riding position of an individual is determined by the size, adjustment and type of bicycle ridden by the individual in the past, this may lead to the selection of the wrong bicycle size, or to adjustments which perpetuate the utilization of a riding position which is inappropriate to the new bicycle, the rider and/or his needs.

In recent years, a great deal of research has been done regarding the dynamics of bicycle riding both as a sport and as a form of recreational exercise. As a result of this research, mathematical relationships have been scientifically derived regarding the optimum dimensions of a bicycle for any particular individual and regarding the preferred riding position for various types of bicycles and levels of intensity of their use. These relationships have been published and may be used in the selection and adjustment of a bicycle provided accurate measurements of various bodily dimensions of the individual who is to use the bicycle are available. The most important of these dimensions are height, weight, crotch height, hand height, knee height, foot length, and shoulder width. Of these, the most difficult to measure accurately, particularly in the retail setting, is crotch height. That measurement requires greater accuracy than that obtainable by, for example, an in-store measurement of an individual's inseam for the purpose of fitting a pair of pants. A more accurate direct measurement of this dimension is not possible, however, without the creation of undue embarrassment to the customer and/or the fitter.

Accordingly, in the past this sensitive measurement was made in the store indirectly by having the customer straddle a bicycle frame having a cross bar of known height. The front wheel of the bicycle then was lifted off the ground as far as possible. The amount by which the front wheel was lifted from the floor was considered to be roughly equal to twice the distance between the known cross bar height and the customer's crotch. Thus, by adding the known cross bar height to one half of the distance the front wheel was raised from the floor in this test, an approximation of the crotch height of the customer was obtained. Alternatively, in some cases the customer was given a wooden dowel and asked to hold the dowel horizontally and "firmly" against his crotch while the fitter measured the distance from the floor to the top of the dowel. Individuals have different interpretations of what constitutes "firmly". They also tend not to hold the dowel so used in an accurately horizontal manner. Accordingly, neither of these prior methods provides a reliable and accurate measurement of the crotch height dimension suitable for use in the scientifically determined bicycle fitting relationships mentioned above.

SUMMARY OF THE INVENTION

It is accordingly an object of the present invention to provide a means for the rapid and accurate measurement of the crotch height of a customer in a retail setting with the least possible embarrassment to the customer and the bicycle fitter.

It is also an object of the present invention to provide an anthropometer suitable for the rapid and accurate measurement of the bodily parameters of individual customers necessary to the selection and adjustment of a bicycle to that customer's needs.

To accomplish these and other objects of the invention, an anthropometer is provided. The anthropometer includes a support means having a vertical upright portion and horizontal crotch height measuring means which is designed to be straddled by the individual to be measured. The crotch height measuring means is slidably mounted upon the vertical portion of the support means, and attached to means for urging it upwardly with a predetermined force.

In a preferred embodiment, the support means includes a platform and a straight tubular element extending vertically upwardly from the platform. The exterior surface of the tubular element may include linear scale means indicating various heights from the upper surface of the platform. The crotch height measuring means includes a horizontal bar attached to a mounting sleeve arranged in slidable engagement with the outer surface of the tubular element. The horizontal bar extends outwardly from the tubular element above the platform. A pulley is located at the top of the tubular upright, and a wire extends from the portion of the horizontal bar adjacent its attachment to the mounting sleeve over the pulley to a counterweight. The counterweight is free to move up and down within the tubular upright. This counterweighting mechanism forms a means for urging the horizontal bar upwardly into the subject's crotch, with predetermined force.

Means for the measurement of other bodily dimensions may also be provided. Thus, the platform may contain transducers for measuring the weight of the customer, and height measuring bars may be slidably mounted upon the tubular upright above and below the crotch bar for measuring the customer's overall height, shoulder height, hand height, and knee height. The customer's foot length similarly can be measured by dimensioned scale means located on the upper surface of the platform.

BRIEF DESCRIPTION OF THE DRAWINGS

These and other features and advantages of the present invention will be best understood by reference to the following detailed description of a preferred embodiment of the present invention and by reference to the attached drawings in which.

DETAILED DESCRIPTION OF PREFERRED EMBODIMENT

Figures 1, 2:
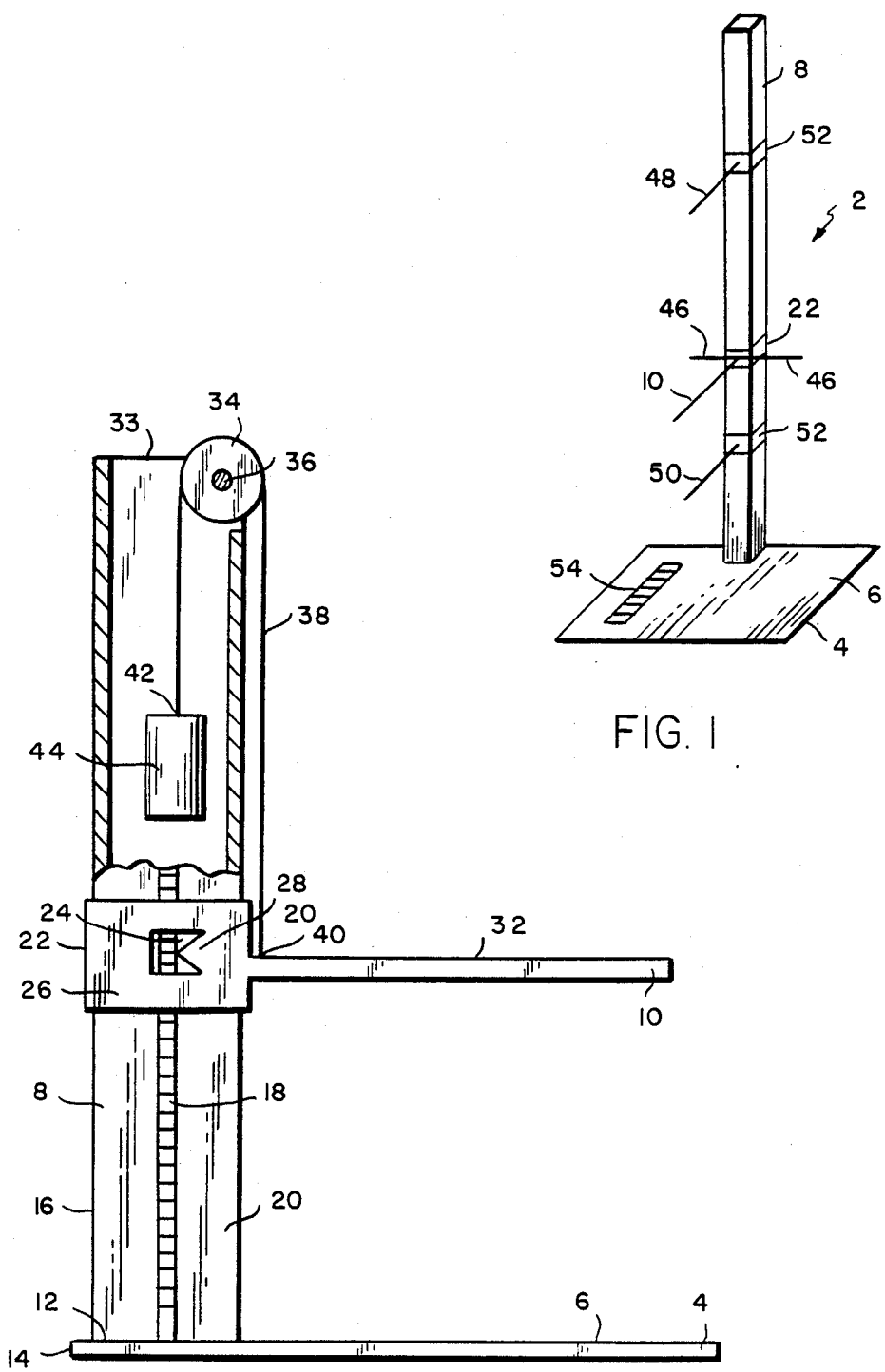
FIG. 1 is a schematic perspective view of an anthropometer in accordance with the present invention.
FIG. 2 is a side view in partial section of an anthropometer in accordance with the present invention.

Referring now to the drawings, and particularly to FIG. 1, there is shown an anthropometer 2 in accordance with the present invention. The anthropometer is specifically adapted for the rapid and accurate measurement of the crotch height of a subject. It includes a platform 4 having a level upper surface 6, a tubular upright 8, and a horizontal crotch height measuring bar 10 slidably mounted to the tubular upright. In the preferred embodiment of the invention, the platform 4 is approximately two feet square. The tubular upright is an aluminum extrusion (for example) which is approximately seven feet long and has a two inch square cross section. The crotch height measuring bar is approximately eighteen inches long, and has a circular cross section. It may be either solid or hollow, and may be formed of wood, metal, or any other suitably rigid material.

As best seen in FIG. 2, the tubular upright 8 is affixed at one of its open ends 12 normally to the upper surface 6 adjacent one of its edges 14. In the preferred case, one of the flat sides 16 of the upright 8 is located parallel the edge 14. A dimensioned scale (i.e., ruler) element 18 is located on side 20 of the tubular element indicating the vertical distance from upper surface 6. The crotch height measuring bar 10 extends horizontally outwardly from a mounting sleeve 22 above the upper surface 6 of the platform 4. Mounting sleeve 22 preferably has a square cross section (for reasons next discussed) and is located in slidable engagement with the exterior surface of tubular upright. The square shape of the tubular upright 8 and of the mounting sleeve 22 act to prevent the sleeve from rotating about the upright. The mounting sleeve also includes a window 24 in its side 26 including a pointer element 28 whose tip 30 is located in the same horizontal plane as the upper edge 32 of the crotch height measuring bar 10. Window 24 allows the operator of the anthropometer to read the height of the top edge of the crotch height measuring bar directly from the scale 18 located on side 20 of the tubular upright. In the event that looseness of the fit between the sleeve 22 and the exterior surface of the tubular element 8 causes binding of the sleeve impeding its free vertical movement or deviations of the crotch height measuring bar from the horizontal, bearing means may be provided between the inner surface of the sleeve and the exterior surface of the tubular element in any well known manner.

Figure 3:
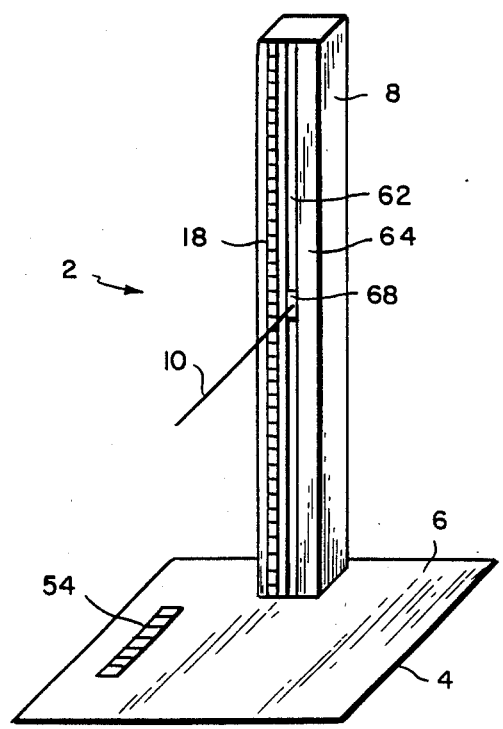
FIG. 3 is a schematic perspective view of another anthropometer in accordance with the present invention; and, FIG. 4 is a partial cross-sectional view of the anthropometer of FIG. 3 showing the crotch height measuring bar attached to a mounting plate slidably located in a longitudinal channel in the upright.
Figure 4:
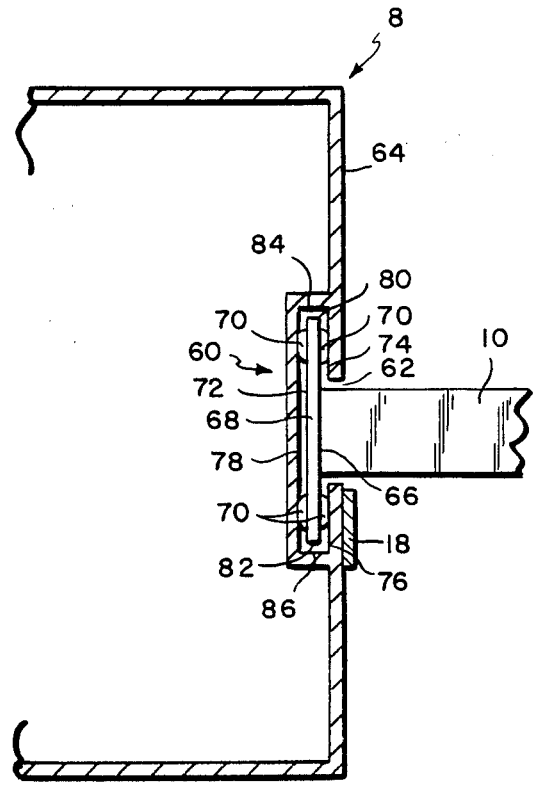

In another embodiment, best seen in FIGS. 3 and 4, the upright 8 includes an longitudinal, generally C-shaped channel 60. The open section of the channel 60 forms a longitudinal slot 62 in the wall 64 of the upright. A mounting plate 68 is slidably located in the channel 60. The crotch height measuring bar 10 extends horizontally from the forward surface 66 of the mounting plate 68 outwardly through the longitudinal slot 62 over the surface 6 of the platform 4. The mounting plate 68 includes bearing means 70, such as wheels or roller bearings, extending outwardly from its forward and rear surfaces 66 and 72 in contact with the adjacent inner surfaces 74, 76 and 78 of the channel 60. Bearing means 70 maintains the horizontal orientation of the crotch height measuring bar 10, and facilitates its vertical movement relative to the upright. In the event that axial twisting of the crotch height measuring bar becomes a problem, similar bearing means may be provided in any well known manner between the left and right edges 80 and 82 of the mounting plate and the surfaces 84 and 86 of the channel 60. The dimensional scale 18 also may be located on the outer surface of the wall 64 adjacent the slot 62 to permit the operator to read height measurements directly by comparing the location of the top edge of the crotch height measuring bar 10 with the adjacent dimensional scale 18.

At the upper end 33 of the upright 8, a pulley 34 is mounted centrally on pin 36. A wire 38 is affixed at one of its ends 40 to the crotch height measuring bar 10 adjacent the mounting sleeve 22. Wire 38 extends vertically upwardly from crotch height measuring bar 10, passes over pulley 34, and extends vertically downwardly into the interior of the tubular element 8. The other end 42 of the wire 38 is attached to counterweight 44, which is free to move vertically within the tubular upright. Of course, counterweight 44 also could be suspended outside the tubular upright, instead.

In use, the crotch measuring bar 10 is pulled downwardly to a horizontal height which is low enough for the subject to straddle comfortably. Thereafter, the subject guides the crotch height measuring bar into engagement with his crotch and releases the bar. The force of the counterweight pulling upon the wire 38 urges the crotch height measuring bar into "firm" engagement with the subject's crotch. This allows consistently accurate measurements of the crotch height to be taken rapidly in a retail setting without embarrassment to either the subject or the individual taking the measurement.

Various modifications and/or additions to the preferred embodiment described will occur to those skilled in the art. For example, the crotch height measuring bar may be provided with handle bars 46 extending outwardly from the bar 10 generally parallel to the upper surface 6 of the platform 4. Handle bars 46 facilitate the guidance of the crotch height measuring bar into engagement with the crotch of the subject by the subject. They may also be used to facilitate the application of upward force to the crotch height measuring bar by the subject himself. In such cases, the pulley/counterweight is not used, and the application of a consistent force by the measuring bar against the subject's crotch is assured by the provision of spring, hydraulic or pneumatic force measuring devices against which the crotch height measuring bar is pulled or pushed by the subject. Similarly, force transducer means (not shown) could be located in the platform 4 to provide an indication of the weight of the subject. Also, horizontal height measuring arms 48 and 50 may be mounted for vertical movement on the tubular element 8. Locating such measuring arms respectively above and below crotch measuring bar 10, provides the capability of accurate and rapid measurement of knee height, hand height, shoulder height, and overall height. Of course, since these measurements may be made without the necessity of applying a force to a surface, the mounting of measuring arms 48 and 50 to tubular element 8 should be such that these arms will not simply slide down the tubular element and/or interfere with the crotch height measurement.

This may be accomplished by the use of mounting sleeves 52 similar to sleeves 22 for each added measuring arm which include means for restricting their vertical movement such as set screws or friction members. In addition, the location of a dimensioned scale 54 on the surface 6 of platform 4 provides an immediately available means for the measurement of a subject's foot length. Finally, means providing an automatic visual display of the various measurements made by the anthropometer and/or the result of the use of those measurements in the mathematical bicycle fitting relationships mentioned above may be utilized with the present invention.

Further modifications, adaptations, and alterations of the concept of measuring the crotch height of a subject with a measuring means which bears against, and is urged against a subject's crotch with a predetermined force, will become apparent to those skilled in the art in view of the above description of a preferred form of the invention. Therefore, it should be understood that the present discussion of the invention has been by way of illustration only. The invention should not be construed as being limited thereby except as specifically set forth in the following claims.

I claim:

1. An anthropometer for determining the crotch height of a standing individual comprising:
    support means including a fixed upright portion;
    first measuring means depending from said upright portion including an upper surface adapted to bear against the crotch of said individual, said upper surface being freely moveable in the vertical direction; and
    means for urging said upper surface upwardly with a predetermined force.

2. The anthropometer of claim 1 wherein said support means comprises (a) a platform having a level upper surface dimensioned to receive the standing individual to be measured and (b) a fixed vertical upright extending upwardly from said platform.

3. The anthropometer of claim 2 wherein means for indicating the foot length of said individual are located on said platform.

4. The anthropometer of claim 1 wherein means for indicating vertical heights are located on said upright portion.

5. The anthropometer of claim 1 wherein said measuring means is a straight, rigid, elongated element, having a circular cross section, small in comparison to its length.

6. The anthropometer of claim 1 wherein said upright portion is tubular, and wherein said means for urging said upper surface of said first measuring means upwardly comprises a counterweight located and freely vertically movable within said upright portion; pulley means located adjacent the top of said upright portion and an elongated, flexible, connecting element having first and second ends, said connecting element being attached at its first end to said counterweight and extending upwardly therefrom, over said pulley, and thence downwardly to its second end, which is connectingly attached to said measuring means adjacent said upright.

7. The anthropometer of claim 1 wherein horizontal hand grip means extend outwardly from opposite sides of said measuring means adjacent said upright.

8. The anthropometer of claim 1 wherein second horizontal measuring means is attached in vertically movable relation to said upright above said first measuring means.

9. The anthropometer of claim 8 wherein third horizontal measuring means is attached in vertically movable relation to said upright below said first measuring means.

* * * * *